(12) United States Patent
Schwägli et al.

(10) Patent No.: US 11,589,926 B2
(45) Date of Patent: Feb. 28, 2023

(54) MOBILE SURGICAL TRACKING SYSTEM WITH AN INTEGRATED FIDUCIAL MARKER FOR IMAGE GUIDED INTERVENTIONS

(71) Applicant: Medivation AG, Brugg (CH)

(72) Inventors: Tobias Schwägli, Solothurn (CH); Jan Stifter, Schneisingen AG (CH)

(73) Assignee: Medivation AG, Brugg (CH)

( * ) Notice: Subject to any disclaimer, the term of this patent is extended or adjusted under 35 U.S.C. 154(b) by 907 days.

(21) Appl. No.: 16/472,191

(22) PCT Filed: Jan. 3, 2018

(86) PCT No.: PCT/EP2018/050095
§ 371 (c)(1),
(2) Date: Jun. 20, 2019

(87) PCT Pub. No.: WO2018/127501
PCT Pub. Date: Jul. 12, 2018

(65) Prior Publication Data
US 2019/0328466 A1 Oct. 31, 2019

(30) Foreign Application Priority Data

Jan. 4, 2017 (CH) .................................. 00005/17

(51) Int. Cl.
*A61B 34/20* (2016.01)
*A61B 90/00* (2016.01)
(Continued)

(52) U.S. Cl.
CPC .............. *A61B 34/20* (2016.02); *A61B 6/547* (2013.01); *A61B 90/39* (2016.02); *G06T 7/246* (2017.01);
(Continued)

(58) Field of Classification Search
CPC . A61B 34/20; A61B 90/39; A61B 2034/2057; A61B 2090/061;
(Continued)

(56) References Cited

U.S. PATENT DOCUMENTS 6,477,400 B1 11/2002 Barrick
6,697,664 B2 2/2004 Kienzle, III et al.
(Continued)

FOREIGN PATENT DOCUMENTS

EP 1868157 A1 12/2007
EP 2245986 A1 11/2010
(Continued)

OTHER PUBLICATIONS

International Application No. PCT/EP2018/050095, International Search Report dated Mar. 27, 2018, 5 pages.

*Primary Examiner* — Kevin T Truong
*Assistant Examiner* — Diana Jones
(74) *Attorney, Agent, or Firm* — Hard IP LLC

(57) ABSTRACT

A mobile surgical tracking system comprises a mobile surgical tracking device comprising an integrated fiducial marker and an imaging device. The imaging device is configured to generate an image of a patient's anatomical structure. The mobile surgical tracking system comprises a tracking system coordinate frame. The integrated fiducial marker has a position which has a known relation to the
(Continued)

tracking system coordinate frame for the direct registration of the image to the coordinate system of the mobile surgical tracking device.

14 Claims, 3 Drawing Sheets

(51) Int. Cl.
　　　*G06T 7/246*　　　(2017.01)
　　　*A61B 6/00*　　　(2006.01)
　　　*A61B 6/14*　　　(2006.01)
　　　*A61B 17/68*　　　(2006.01)
　　　*A61B 17/00*　　　(2006.01)
(52) U.S. Cl.
　　　CPC ............... *A61B 6/14* (2013.01); *A61B 17/68* (2013.01); *A61B 2017/00734* (2013.01); *A61B 2034/2057* (2016.02); *A61B 2090/061* (2016.02); *A61B 2090/365* (2016.02); *A61B 2090/3764* (2016.02); *A61B 2090/3916* (2016.02); *A61B 2090/3945* (2016.02); *G06T 2207/10116* (2013.01); *G06T 2207/30008* (2013.01); *G06T 2207/30204* (2013.01)
(58) Field of Classification Search
　　　CPC ...... A61B 2090/365; A61B 2090/3764; A61B 2090/3916; A61B 2090/3945; A61B 6/14; A61B 17/68; A61B 2017/00734; G06T 7/246; G06T 2207/10116; G06T 2207/30008; G06T 2207/30204
　　　See application file for complete search history.

(56) References Cited

U.S. PATENT DOCUMENTS

| | | | |
|---|---|---|---|
| 6,932,506 B2 | 8/2005 | Mitschke et al. | |
| 7,117,027 B2 | 10/2006 | Zheng et al. | |
| 7,130,676 B2 | 10/2006 | Barrick | |
| 7,139,418 B2 | 11/2006 | Abovitz et al. | |
| 7,570,791 B2 | 8/2009 | Frank et al. | |
| 2003/0073901 A1 | 4/2003 | Simon et al. | |
| 2006/0173269 A1* | 8/2006 | Glossop | A61B 5/06 600/407 |
| 2008/0064947 A1 | 3/2008 | Heruth et al. | |
| 2008/0319491 A1 | 12/2008 | Schoenefeld | |
| 2013/0274633 A1 | 10/2013 | Hladio et al. | |
| 2014/0005527 A1 | 1/2014 | Nagarkar et al. | |
| 2014/0049629 A1 | 2/2014 | Siewerdsen et al. | |
| 2018/0049808 A1* | 2/2018 | Krimsky | A61B 8/085 |

FOREIGN PATENT DOCUMENTS

| | | | |
|---|---|---|---|
| EP | 2436333 A1 * | 4/2012 | ............ A61B 34/20 |
| EP | 2436333 A1 | 4/2012 | |
| EP | 2468207 A1 | 6/2012 | |
| EP | 2793042 A1 | 10/2014 | |
| EP | 2868277 A1 | 5/2015 | |
| EP | 3162316 A1 | 5/2017 | |
| WO | 2011020505 A1 | 2/2011 | |
| WO | 2013164770 A2 | 11/2013 | |
| WO | 2016139638 A1 | 9/2016 | |

* cited by examiner

MOBILE SURGICAL TRACKING SYSTEM WITH AN INTEGRATED FIDUCIAL MARKER FOR IMAGE GUIDED INTERVENTIONS

This application is a U.S. national stage filing under 35 U.S.C. 371 of international patent application no. PCT/EP18/050095, filed on Jan. 3, 2018, which claims priority to Swiss patent application no. CH00005/17, filed on Jan. 4, 2017, the contents of both of which are incorporated herein by reference in their entirety.

TECHNICAL FIELD

The invention is related to a mobile surgical tracking system comprising a mobile surgical tracking device comprising an integrated fiducial marker for the direct registration of radiographic images to the tracker's coordinate system. The mobile surgical tracking device can be configured as a miniaturized tracking device with the integrated fiducial marker for image guided interventions. This allows a simpler and more accurate measurement setup in a large number of computer assisted surgical applications where the registration of radiographic images to a patient reference frame is required. Single or multiple images may be acquired preoperatively, including conventional X-ray, CT scan, cone beam CT scan, or intra-operatively using single or multiple C-Arm images with the tracking device fixed at a known relation to the patient's anatomy. The fixation can either be made to fit on an external surface of the patient or through a minimal invasive type of fixation through an incision. A direct registration of the recorded images or image-volume of the patient's anatomy to the tracking system is possible with the integrated radio-opaque fiducial marker in the tracking device. In such a setup there is no need for an external tracking system to track the position of the imaging equipment in relation to the patient. With a conventional system, often problems arise with large sized tracking markers that must be attached to the patient. Consequently, line-of-sight issues occur very frequently with prior art surgical tracking systems.

DESCRIPTION OF RELATED ART

Mobile, instrument or patient mountable tracking systems are described for surgical navigation in US2008319491 A1 and US 20130274633 A1. The tracking system of US2008319491 A1 is part of a surgical navigation system and locates and tracks arrays in real-time. The positions of the arrays are detected by cameras and displayed on a computer display. The tracking system is used to determine the three-dimensional location of the instruments which carry markers serving as tracking indicia. The markers may emit light, in particular infrared light or reflect such light. The light is emitted or reflected to reach a position sensor for determining the position of the instrument. The specific anatomical structure of the patient can be characterized by a limited number of landmarks, which can be used to generate a virtual patient specific instrument. The virtual patient specific instrument can be used to manufacture a patient specific instrument, e.g. by means of rapid prototyping. Such a patient specific instrument can be positioned on the patient's bone structure accurately and attached to the patient's bone structure. The patient specific instrument can include a tracking device, e.g. a reference array. The position of the reference array is thus known and can be used to position the patient specific instrument virtually on the display. Due the fact that rigid reference arrays can be obtained, the patient's bone structure can be tracked without the need of additional rigid array markers. The navigation system automatically recognizes the position of the reference array relative to the patient's anatomy. A system for performing a computer-assisted hip replacement surgery is disclosed in document US2013/0274633. The system comprises a pelvis sensor, a broach sensor and a femur sensor coupled to the respective bone or broach structure. The position of the sensors is recorded during the surgery by a processing device. The processing device can perform a femoral registration by measuring an orientation between the broach sensor and the femur sensor. The processing device can display a fixed target frame and a track frame, which can be matched by adjusting the positions of the bone and broach structures and when the matching position is reached, the change in leg length and a change in offset can be calculated. Each of the sensors can be configured as an optical reader or a beacon. These two documents relate thus to the concept of a miniaturized and mobile tracking system and their applications in surgical procedures.

The tracking system can also be used for multiple surgical interventions like orthopedics, trauma and spine surgery where tracking of an instrument relative to a single or multiple acquired C-Arm image is desired and can help to reduce the radiation dose in such interventions. This setup is described as virtual fluoroscopy for several applications (U.S. Pat. Nos. 6,697,664 B2, 6,932,506 B2, 7,130,676 B2, 7,139,418 B2, US20030073901 A1). In a state of the art setup for virtual fluoroscopy the C-Arm imaging device needs to be equipped with a trackable reference frame and the imaging parameters must be calibrated with respect to this reference frame. An additional optical marker has to be positioned in a fixed position with respect to the patient or fixed to the patient and to the instrument for the intervention (e.g. a drill sleeve). Such a setup is complex in a surgical theater and requires always a line of sight to all tracked devices. For example, the Brainlab X-Spot device according to EP2245986 B1 is an x-ray marker device comprising an arrangement of x-ray markers defining device straight lines forming the edges of pyramids. This x-ray marker device allows to register the patient anatomy to a tracker fixed to the patient using a special tracker with fiducial marker elements, but still requires an external tracking system. Other solutions (US2014049629 A1) propose to attach a tracking system to the C-Arm to limit the line-of-sight issues and omit the step of tracking the C-arm position. The C-arm imaging device can track the external environment with respect to the coordinate system fixed to the C-arm.

A problem associated with any of these prior art solutions is to integrate the surgical tracking device into the anatomical structure model generated from the images of the imaging device. The surgical tracking device can be a mobile surgical tracking device, such as an implant, a surgical instrument or a patient specific instrument. This integration requires complex coordinate transformation calculations to match the coordinate system(s) of the tracked device with the respective coordinate systems of the imaging device to determine the exact position of the tracked device both in the anatomical structure model and at the same time in the anatomical structure itself.

There is thus a need for a simplified tracking system for tracking the position of a surgical tracking device by integration into the model of the anatomical structure obtained from the radiographic images generated by the imaging device.

If the term «for instance» is used in the following description, the term relates to embodiments or examples, which is not to construed as a more preferred application of the teaching of the invention. The terms "preferably" or "preferred" are to be understood such that they relate to an example from a number of embodiments and/or examples which is not to construed as a more preferred application of the teaching of the invention. Accordingly, the terms "for example", "preferably" or "preferred" may relate to a plurality of embodiments and/or examples.

The subsequent detailed description contains different embodiments of the mobile surgical tracking system according to the invention. The mobile surgical tracking system can be manufactured in different sizes making use of different materials, such that the reference to a specific size or a specific material is to be considered as merely exemplary. In the description, the terms «contain», «comprise», «are configured as» in relation to any technical feature are thus to be understood that they contain the respective feature, but are not limited to embodiments containing only this respective feature.

SUMMARY OF THE INVENTION

The object of the invention is solved by mobile surgical tracking system comprising a mobile surgical tracking device comprising an integrated fiducial marker and an imaging device, whereby the imaging device is configured to generate an image of a patient's anatomical structure, whereby the mobile surgical tracking system comprises a tracking system coordinate frame. The integrated fiducial marker has a position which has a known relation to the tracking system coordinate frame for the direct registration of the image to the coordinate system of the mobile surgical tracking device. The image can be in particular a radiographic image. The anatomical structure can in particular be a bone structure.

Instead of locating the mobile surgical device in the model of the anatomical structure and in the anatomical structure of the patient, which requires complex calculations to match the coordinate systems of the surgical tracking device, the virtual surgical tracking device, the imaging device and the model of the anatomical structure generated by the imaging device required by the approach taken in the prior art solutions it is possible with the mobile surgical tracking system of the invention to directly register the image with the mobile surgical tracking device. The image is integrated into the mobile surgical tracking system coordinate frame, whereby the position of the mobile surgical tracking device with respect to the anatomical structure both virtually, thus in the anatomical structure model, and physically, thus in the anatomical structure of the patient is simultaneously defined.

In other words, a direct registration of the acquired images to the tracking system reference frame can be achieved by the proposed solution of a miniaturized tracking system with integrated fiducial marker according to the invention. Such a registration can be more accurate as no transformation over a multiple coordinate system requiring multiple relative measurements of different trackers has to be made. The mobile surgical tracking device can comprise an instrument, such as a surgical instrument, a surgical tool, a patient specific instrument, an implant or combinations thereof. The instrument to be guided can be equipped with an optical marker which is directly measured in the target coordinate system of the tracking system. As the tracking system is attached directly at the site of intervention and the instrument is in close range of the tracking system, there are no line of sight issues as with existing external optical tracking solutions.

Other applications for the described invention are for example in the field of orthopedics, spine, cranial/neuro, ENT (ear, nose, throat), dental navigation or any other image guided surgical intervention. The mobile surgical tracking device can be used for image guided interventions where a CT or cone beam CT scan is acquired pre-operatively. The mobile surgical tracking device can be attached in a known positional relationship with respect to the patient close to the surgical field. According to this configuration, the scan can be made by integrating the integrated fiducial marker into the imaging volume. Thereby a direct registration of the imaging device coordinate frame to the patient coordinate frame is possible. Either the mobile surgical tracking device can be left on the patient until the surgical procedure is carried out or the mobile surgical tracking device can be fixed at the same location for the surgical intervention.

An application of the proposed invention includes a dental image based navigation system. A cone beam CT is made with the mobile surgical tracking device and the integrated fiducial marker mounted on the patient teeth using a dental tray. Later the mobile surgical tracking device can be attached at the same location or position as during the CT scan and the dental drill can be navigated relative to acquired image data or computed 3D reconstructions.

In another embodiment the proposed mobile surgical tracking system can be used for intraoperative registration of pre-operatively acquired images like a CT or MRT scan of the patient's anatomy. This is described for example in U.S. Pat. No. 7,570,791 B2 using an external optical tracking system. By using multiple C-Arm images with the proposed tracking system in place, a registration of the preoperative images in relation to the intraoperative acquired radiographic images can be made.

In another application, the proposed mobile surgical tracking system can be used for intraoperative calculation of 3D models of the patient anatomy based on a single or multiple 2D radiographic image acquisition. This is described for example in U.S. Pat. No. 7,117,027 B2 or EP 1868157 A1 using an external optical tracking system. Using multiple C-Arm acquisitions with the proposed tracking system in place such a 2D-3D registration can be implemented and direct navigation of surgical tools in relation to these calculated 3D models is possible. Due to the small size of the tracking device and trackable marker the fixation to the patient can be made less invasive and closer to the surgical site.

According to an embodiment, the integrated fiducial marker comprises a computer detectable element, whereby the computer detectable element is detectable in the image, whereby the computer detectable element can be selected from the group of spheres, line segments, circles, ellipses, helices, patterns, holes or any combination thereof, whereby the image comprises an image coordinate frame or an image projection to allow the registration of the image coordinate frame or the image projection to the mobile surgical tracking system coordinate frame.

Integrated fiducial markers as described in this document always require a configuration of single or multiple geometrical elements that allow to register an image or image volume with respect to the coordinate frame of the mobile surgical tracking system including the integrated fiducial marker. The use of an integrated fiducial marker for the calculation of perspective projection parameters of a C-arm position can be beneficial for a great number of surgical applications. Another embodiment of such integrated fiducial markers are configurations for the registration of image volumes generated with conventional CT scanners of cone beam CT scanners (CBCT).

Depending on the type of registration and registration accuracy required, the size and geometry of the integrated fiducial marker can be variable. In some implementations, the integrated fiducial markers comprise a number of radio-opaque spheres in a known spatial relationship. According to some embodiments, the integrated fiducial markers can be made of stainless steel, thus they can be specifically configured as spherical marker elements. An advantage of such spherical marker elements is their simple detection in radiographic images. In addition thereto, spherical marker elements are always visible as circles in the images. Other possibilities for integrated fiducial markers include line segments, elliptical lines or helical lines made from radio-opaque material. Also, additional elements/symbols such as arrows, concentric circles, letters, can be added to automatically identify the orientation of the marker or elements of the integrated fiducial marker. Alternatively, the integrated fiducial marker can be made from a radio-opaque material with a defined outer geometry and with holes at a given positions. The detection of outline edges, corners and holes can be made in radiographic images for fiducial detection. An integrated fiducial marker could also be configured as a pattern of transparent and opaque regions. Any combination of the described types of integrated fiducial markers is possible in combination with a mobile surgical tracking device.

According to an embodiment, the integrated fiducial marker is integrated in a printed circuit board (PCB) containing tracking system electronics. The printed circuit board (PCB) can comprise one of a single PCB, a multi-layer PCB, a plurality of PCBs, a flexible PCB. Alternatively or additionally, the integrated fiducial marker can be incorporated into the housing of the mobile surgical tracking device with a known relation to a coordinate frame of an optical tracking element.

The integrated fiducial marker can be integrated into a patient fixation device or can be attached to the patient fixation device. The mobile surgical tracking device can be attached to the integrated fiducial marker in a defined spatial position. In particular, the patient fixation device has a geometry usable as the integrated fiducial marker, such that the mobile surgical tracking device can be attached in a known position on the mobile surgical tracking device, e.g. an instrument, a surgical instrument, a patient specific instrument, a surgical tool.

The integrated fiducial marker may be integrated into the mobile surgical tracking device, but other embodiments are also possible and preferable for some applications. In one embodiment, the integrated fiducial marker and the mobile surgical tracking device are detachable. Thereby, the imaging can be made when the mobile surgical tracking device is removed. If the mobile surgical tracking device is temporarily removed, no artifacts from the mobile surgical tracking device become part of the images. According to this configuration, the mobile surgical tracking device does at least temporarily not interfere with the imaging device. Furthermore, a detachable mobile surgical tracking device would allow to use the integrated fiducial marker for imaging only and to use the mobile surgical tracking device only in the surgical intervention. Even more, it may be preferable for the surgical intervention to remove the integrated fiducial marker from the mobile surgical tracking device as the space used for the integrated fiducial marker may interfere with surgical tool path or other surgical procedure. Possible configurations comprise at least one of a detachable mobile surgical tracking device and a detachable integrated fiducial marker. If both the mobile surgical tracking device and the integrated fiducial marker are attachable to the same mechanical interface interchangeably, they could be mounted to a patient fixation device at the same positions, e.g. first the integrated fiducial marker for imaging and then the mobile surgical tracking device for surgical intervention.

In another embodiment, the integrated fiducial marker is formed by the patient fixation device itself, for example an external fixation device like a taylor spatial frame. In this setup, the fixation device itself has a geometric structure that is detectable in the images, in particular radiographic images, and can be used to calculate image registration. The mobile surgical tracking device can be mounted at a known position to this patient fixation device and like this to the integrated fiducial marker formed by the instrument fixation. For example, two frames in a taylor spatial frame application can be mounted to two bone segments and x-ray images from multiple directions can be made. A mobile surgical tracking device can be attached at one frame and on the other frame a trackable marker can be attached. Based on the x-ray images, the bone segments could be reconstructed as 3D models and fracture reduction could be planned and applied by the taylor spatial frame. The movements of the two fixation devices relative to each other can be tracked by the attached mobile surgical tracking device. According to a preferred configuration, the fixation devices comprise fixation rings. It is possible that additional fiducial elements are added to an existing patient fixation device to be able to use it as the integrated fiducial marker. The additional fiducial elements could be for example part of the attached mobile surgical tracking devices.

The mobile surgical tracking device according to any of the preceding embodiments is preferably lightweight to be mountable to a patient or fixed to an anatomical structure like a bone. Also, a small size is required not to interfere with imaging.

In an embodiment, the mobile surgical tracking system comprises an integrated optical tracking system.

In one embodiment the optical tracking system could be implemented as a stereo- or multi-camera optical system. The optical tracking system can be used for tracking an active or passive marker. Such systems are known and well described but based on the required optics and computation tasks for tracking, an integration to a very small form factor is not straightforward. Alternatively, a single camera tracking system could be provided, as this system would require less space, but the achievable accuracy of this system is limited.

The integrated optical tracking system can comprise a shadow imaging tracking, e.g. using a shadow mask above an imaging sensor in order to track the position of a marker equipped with three or more LEDs in a known configuration. In a preferred embodiment a shadow imaging technology is used as tracking system in the mobile surgical tracking device. This tracking system only requires an optical sensor, for example a CCD chip with a shadow mask on top of it and the computation can be implemented by a small size embedded system. It is possible to integrate all components in a single chip for further reduction of the possible form factor. The trackable elements require at least 3 LEDs in a known spatial configuration that are measured by the shadow imaging system. With the single LED position, the tracking system can compute the 6D position of the trackable element. Another advantage of the shadow imaging tracking is its large opening angle of 120° or more, which is a substantial advantage for close range measurements as also intended with this invention. The principle of shadow imaging (EP 2793042 A1) and its integration with surgical instruments (EP15192564 A1) is described in previous patent applications and other publications, which are incorporated by reference in their entirety into this application.

In a preferred embodiment, the mobile surgical tracking system comprises a battery. In particular, the mobile surgical tracking device is battery driven and can operate completely wireless.

The mobile surgical tracking system can comprise a display device which can be configured to implement a wireless communication. The display device can be configured to retrieve preoperatively acquired tracking data, image data, planning data or other patient data stored in a memory of the mobile surgical tracking device. According to an embodiment, the display device comprises an augmented reality display device.

The tracking data can be transferred to a display device that guides the surgical intervention over a wireless link as for example Bluetooth LE. The battery operation should allow for tracking during a surgery normally for at least some minutes up to several hours. The battery can either be replaceable or rechargeable. For some applications it could be preferable to have a single use device that could only be used for one single surgery. For other applications, a resterilizable tracking system could be preferable. The highly integrated design of the mobile surgical tracking system according to any of the embodiments allows to produce a mobile surgical tracking device and trackable elements so that they can be used as single use devices. The display device computes and shows the instrument position in relation to the image data or generated data thereof. The display device may be one of a computer including a display or a smartphone or a tablet device. The information could be shown to the surgeon through wearable smart glasses instead of using a display device.

According to a further implementation, an augmented reality display device can be used for tracking the wearable position by the measurement system or an additional tracking system. In particular, the model of the anatomical structure model generated from the images generated by the image device can be combined with the patient's anatomical structure and/or the mobile surgical tracking device. The images or any anatomical structure model generated from the images can be matched directly with the patient, in particular, the anatomical structure of the body part which has to be treated by the surgery.

According to an embodiment, the image can be imported to the display device such as a tablet or a smartphone by taking a photo of C-Arm image with the display device.

According to an embodiment, the mobile surgical tracking device and a trackable device can both comprise integrated fiducial markers or only the trackable device can comprise an integrated fiducial marker, whereby the integrated fiducial marker can be attached to an anatomical structure and the mobile surgical mobile tracking device can be attached to the surgical instrument.

According to an embodiment, a plurality of mobile surgical tracking devices can be attached to a plurality of anatomical structures, whereby each mobile surgical tracking device can be equipped with trackable elements so that each mobile surgical tracking device can act as the tracker and/or a trackable device.

According to an embodiment, the mobile surgical tracking system comprises multiple optical tracking systems integrated to allow measurement in multiple directions, whereby each of the optical tracking systems can comprise a measurement volume, whereby at least one of the optical tracking systems can be separate or at least two of the optical tracking systems can be overlapping.

According to an embodiment, the imaging device comprises a radiographic imaging device, whereby the radiographic imaging device can be equipped with optical markers (LED) so that the position of the radiographic imaging device relative to the mobile surgical tracking device can be measured.

BRIEF DESCRIPTION OF THE DRAWINGS

The invention will be explained in more detail in the following with reference to the drawings. There are shown in a schematic representation in.

DETAILED DESCRIPTION

Figure 1:
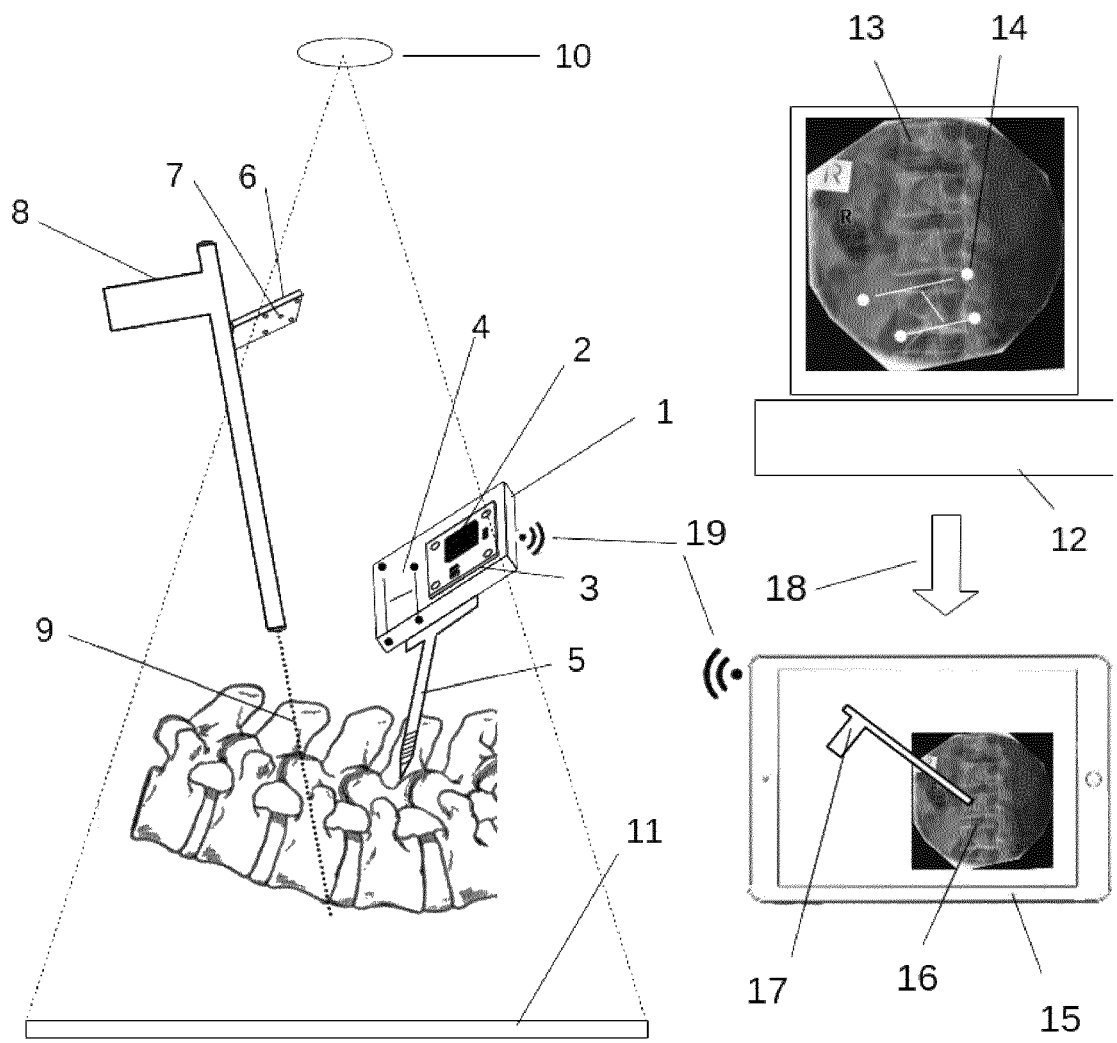
FIG. 1 schematic view of a mobile surgical tracking system according to a first embodiment of the invention, FIG. 2 a detail of the mobile surgical tracking device of FIG. 1, FIG. 3 a view of a mobile surgical tracking system according to a second embodiment of the invention, FIG. 4 a view of a mobile surgical tracking system according to a third embodiment of the invention.

In FIG. 1, a first embodiment of the mobile surgical tracking system 1 of the invention is shown. The small sized mobile surgical tracking system 1 is mounted on a an anatomical structure, in particular a bone structure 9 such as for example multiple vertebrae. This fixation device 5 can be one of a single or multiple bone screws, a pin fixation, clamps or other means for fixing the mobile surgical tracking device in a stable position to the desired bone. The mobile surgical tracking system 1 comprises the following elements: an optical tracking system 2, a printed circuit board with processing unit, a wireless communication unit and an attached battery 3, an integrated fiducial marker 4, in particular a radio opaque fiducial marker, for registration of the radiographic images. Through a radiographic projection from an X-Ray source 10 to the detector panel 11 a radiographic image 13 is generated. In a preferred embodiment, such images are acquired after mounting the mobile surgical tracking system 1 using a C-Arm intraoperatively. The image is transferred from the image acquisition and storage unit of the C-Arm 12 using a defined protocol 18 to the mobile computation unit 15 that shows the navigation screen to the surgeon. In a preferred embodiment, the mobile computation unit 13 and display is a smartphone or tablet device that already provides wireless communication protocols 18, 19 for data exchange. In another embodiment the transfer of the image from the C-Arm scanner to the mobile device could be by taking a photo of the C-Arm screen by means of the integrated camera in the mobile device. In such a setup an image distortion and rectification have to be applied to the image.

For the registration of the radiographic image to the mobile surgical tracking system a coordinate frame 14 of the integrated fiducial marker 4 can be used. Multiple known applications describe how to calculate the perspective projection from integrated fiducial markers 4 in a radiographic image 27. The integrated fiducial markers 4 are detectable by a computer algorithm implemented on the display or navigation device. Once the relation from the image to the coordinate frame 14 of the mobile surgical tracking system 1 is known, an instrument 8, such as a surgical instrument, can be tracked and visualized by a visualization element 17 in the image space 16. The instrument 8 in this embodiment is equipped with an optical marker 6 of at least four LEDs 7 and the tracking system 1 implements a shadow imaging technology as described above to calculate the 6 DOF position of the optical marker 6 and the instrument 8, here a drill sleeve. In another embodiment, the optical tracking could be implemented also using a conventional single camera tracking system with lenses to track an optical marker 6. The optical marker 6 can be one of the group including an active or passive optical marker. An active optical marker can be configured as a light-emitting marker, e.g. a LED. A passive optical marker comprises a reflecting surface. A passive optical marker can in particular include a sphere capable of receiving a light beam, which can be used for measurement purposes. In another embodiment, a small-scale stereo-camera system could be integrated into the mobile surgical tracking system 1 to track optical markers 6. The advantage of the shadow imaging technology is that it can be implemented in a very small form factor which is in particular less than 5×5×2 cm and very lightweight, in particular less than 50 grams.

Figure 2:
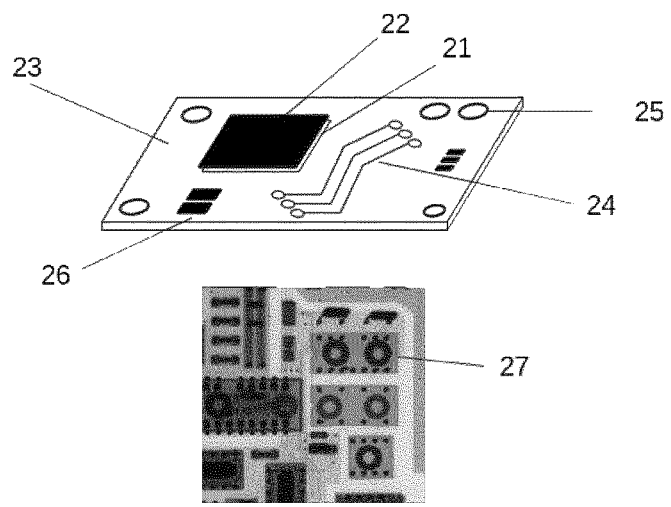

FIG. 2 shows a possible implementation of a mobile surgical tracking device 25 with integrated fiducial markers 4. In this embodiment the integrated fiducial markers 4 are formed as an integral part of a printed circuit board 23. The mobile surgical tracking device 25 includes a shadow imaging device comprising an image sensor 21 and a shadow mask 22. The integrated fiducial markers 4 can either be commonly available electronic components 26, conductive tracks 24 forming a defined pattern on the circuit board, radio-opaque elements placed on the printed circuit board 23, radio-transparent holes in the printed circuit board 23, or any combination thereof. The integrated fiducial markers 4 placed on the printed circuit board form can be detected in the radiographic image 27. Different elements may have different radiographic properties, such as transparent, opaque, semi-transparent. The placement of the integrated fiducial markers 4 can be made as integral part of PCB during board production. Alternatively or additionally, the integrated fiducial markers 4 can be very accurately placed for example through a SMT (surface mount technology) placement machine.

The position of the integrated fiducial markers coordinate system to the tracking system coordinate system can either be guaranteed by very accurate production, placement of the components or by a factory registration method where the spatial relation (6DOF) is defined. The spatial relation can be stored in the memory of the mobile surgical tracking system. In further embodiments, the integrated fiducial markers 4 could be embedded on multiple PCB layers or multiple PCBs to form a three-dimensional arrangement. Such a three-dimensional arrangement of the integrated fiducial markers 4 allows for a more accurate registration of the radiographic images to the mobile surgical tracking system 1 and is preferred if for example C-Arm images are taken from different positions. In a further embodiment, the mobile surgical tracking system 1 can be made very small or even integrated in a single chip and the integrated fiducial markers 4 and this chip itself can include some integrated fiducial markers 4 or a certain geometric shape for detection in radiographic images. In a further embodiment, the integrated fiducial markers 4 could be placed on a flexible PCB where the flexible PCB is mounted in a housing this would also allow for two or preferably a three-dimensional arrangement of the LED by bending of the flexible PCB. In a further configuration, only the measurement system is mounted on a PCB that is placed at a defined position in a radio-transparent housing with integrated fiducial markers 4. Such a configuration is preferred when a large-sized integrated fiducial marker 4 is required, for instance of a size of 5-10 cm and the measurement system and PCB is to be kept very small.

Figure 3:
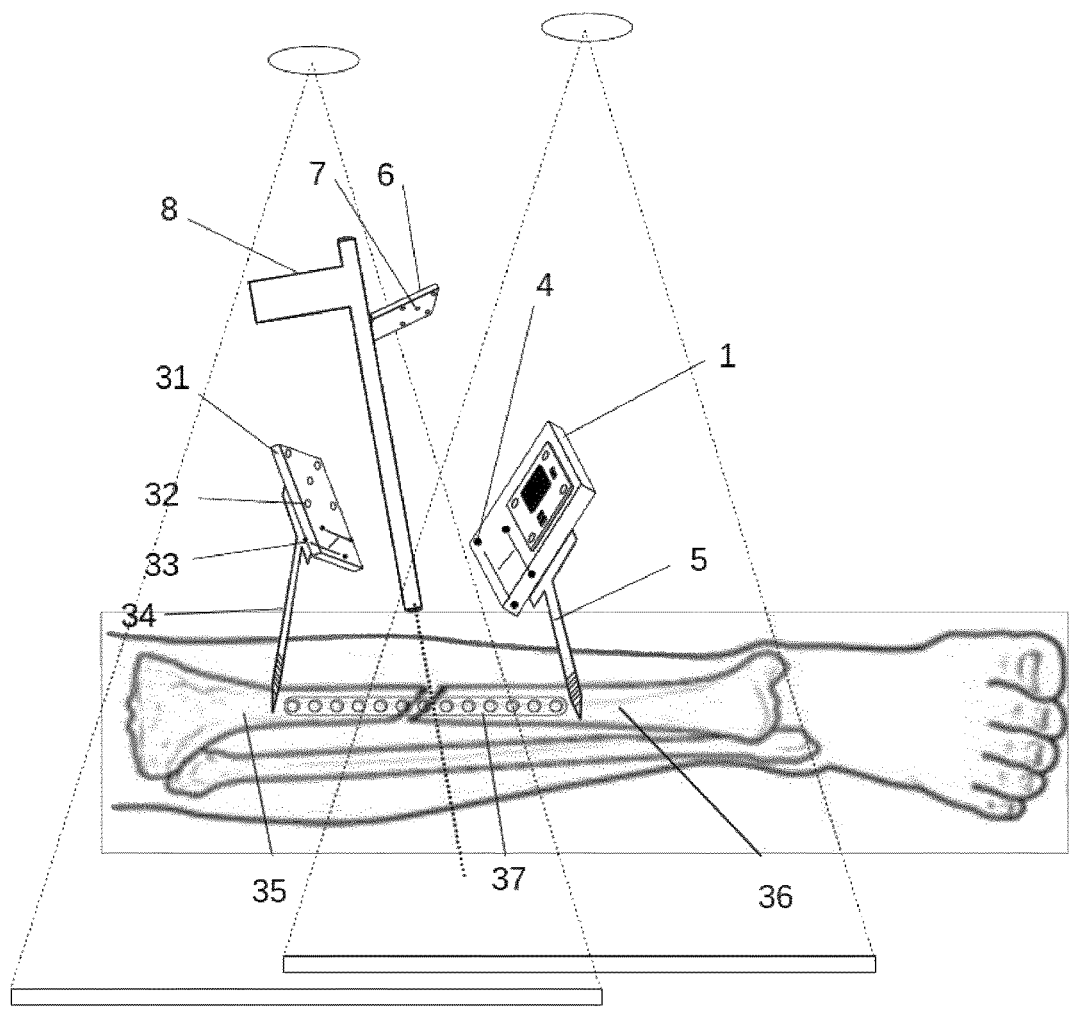

FIG. 3 shows a mobile surgical tracking system 1 according to a second embodiment comprising an integrated fiducial marker 4 rigidly attached with a fixation device 5 to a first bone structure 36 and in addition an optical marker 31 also equipped with an integrated fiducial marker 33 rigidly attached by an attachment element 34 on a second bone structure 35. The setup allows registration of one or multiple radiographic images, such as C-Arm, of the first bone structure 36 to the mobile surgical tracking system 1 mounted on the first bone and registration of one or multiple radiographic images 27 of a second bone structure 35 to the trackable optical marker 31 mounted on the second bone structure 35. This allows to calculate and display movements of the two-bone structure 35, 36 with respect to each other and display the movements to the surgeon. By taking multiple C-Arm images, 3D models of the bone fragments can be established with their spatial locations relative to the reference coordinate systems of the mobile surgical tracking system 1 and trackable optical marker 31. Such a setup could be preferably used for fracture reduction in trauma applications. Additionally, the system could measure the position of placed instruments 8 and implants in the radiographic images, for example trauma plates 37, intramedullary nails, screws. In addition, one or multiple instruments 8 equipped with optical markers 6 can be tracked relative to images of the first or second bone generated 3D reconstructions of the two bones. Also, the instrument position can be tracked to implant feature like for example plate hole positions. The optical marker 6 may also be included in the handle to set the trauma, this would allow to track the plates position on the anatomical, in particular bone structures during placement. In another embodiment, a plurality of mobile surgical tracking systems 1 are mounted on both bones that are also optical markers 31, thereby allowing both bones to be tracked to each other and the instrument 8 to be tracked directly to both bones. In another embodiment, the mobile surgical tracking system 1 can comprise a plurality of optical tracking systems 2 integrated to track multiple measurement volumes in different directions for tracking instruments in multiple locations with respect to the mobile surgical tracking system 1. In a surgical setup it may be necessary to track one instrument on one side of the mobile surgical tracking device, for example a drill sleeve, while the plate handle to insert the plate is located on the opposite side of the mobile surgical tracking device. In on such setup, two tracking systems could be integrated pointing in opposite directions or any other configuration of two or more tracking systems to cover the required measurement volume.

Figure 4:
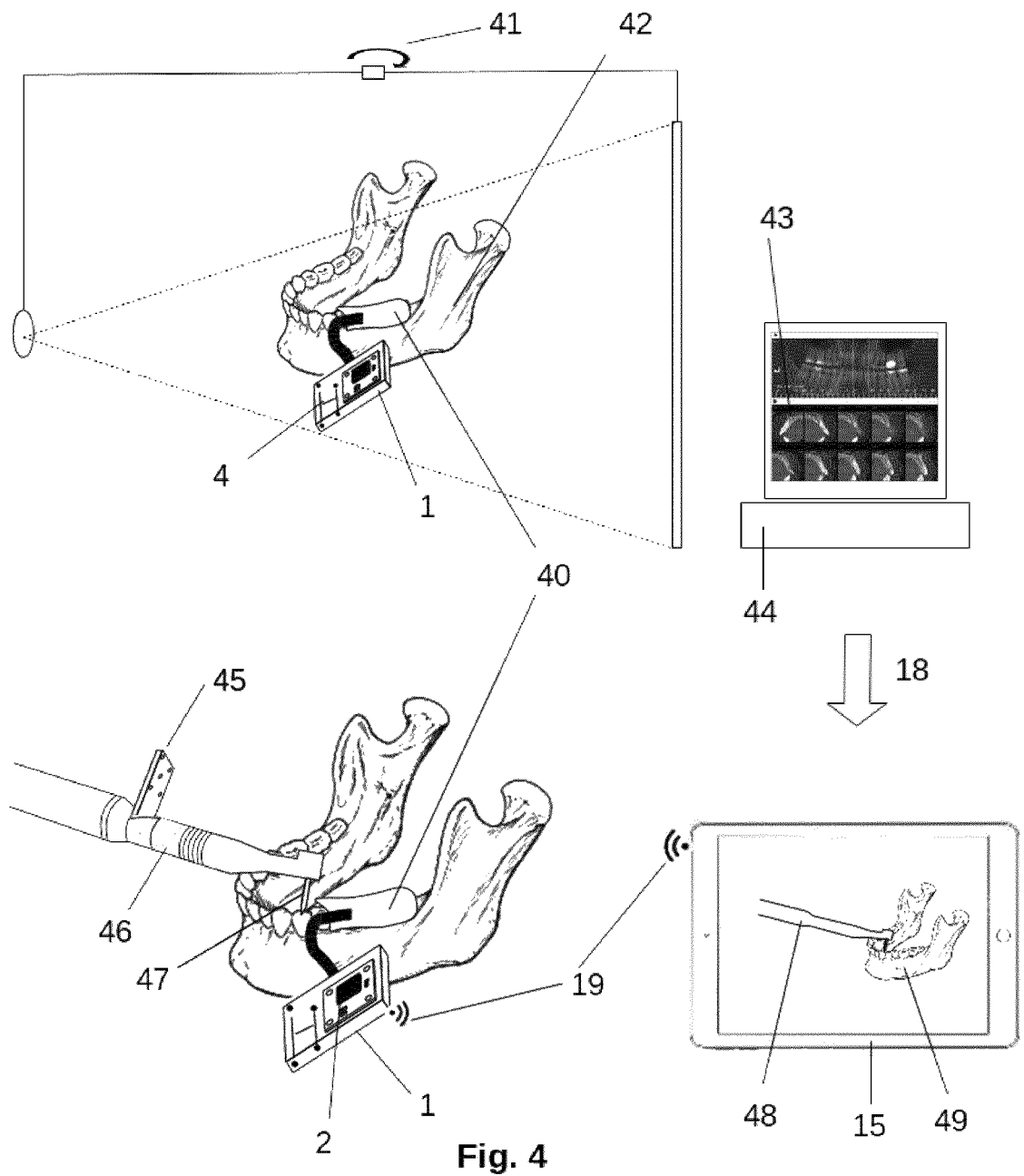

FIG. 4 shows a mobile surgical tracking system according to a third embodiment in a setup for a dental application where the mobile surgical tracking system 1 is temporarily attached to jaw and teeth 42 using a dental tray 40. The fixation can for example be achieved through molding of the teeth structure with a suited molding material. The dental tray 40 must allow to fix the mobile surgical tracking device later in the surgical intervention at the same spatial location relative to the jaw and teeth 42. With the mobile surgical tracking device including the integrated fiducial marker fixed to the patient a cone beam CT scan 41 is carried out and the image volume 43 is saved on the scanner 44. Based on the image volume a planning of dental implant positions can be carried out on the single slice images or based on a 3D visualization of the jaw and teeth 42. Preferably, a dedicated dental planning software is used, and the planned values and image volume are transferred to the mobile computation unit 15 including the display device. The mobile computation unit can include one of a computer unit with display, a smartphone or a tablet device. The mobile computation unit imports the planning data and image data from the CBCT scan and dental planning software. For the intervention, the dental hand piece 46 with the drill 47 is equipped with an optical marker 45, the position of the drill to the optical marker is either known a priori, e.g. pre-calibrated, or registered during the intervention. The mobile surgical tracking device is attached with the dental tray 40 at the same position as during imaging procedure and the position of the image volume 43 and a reconstructed 3D model 49 is known through the integrated fiducial marker 4 in the image volume 43. In an initial step the software identifies the integrated fiducial marker 4 in the image volume 43 and computes the registration transformation from the image coordinate frame to the tracker coordinate frame. Using this transformation and the position of the hand piece measured through the optical marker, the drill position 48 can be displayed relative to the reconstructed 3D model 49 and image volume on the display unit. In a preferred embodiment the mobile surgical tracking device is operated battery driven and communicates the tracking data to display unit using wireless communication as for example through Bluetooth LE (low energy). In another embodiment such a setup could be used for ENT, interventional radiology and other applications where the mobile surgical tracking device is fixed to the head or another part of the body of the patient and a CBCT scan is done. In other embodiments of the invention, a conventional CT scanner could be used. Also, an application with a MRI (magnet resonance imaging) scanner is possible. In this configuration, the integrated fiducial marker 4 must be designed to be detectable in MRI images and the mobile surgical tracking device has to be either compatible with MRI imaging or detachable from the integrated fiducial marker 4 during the imaging procedure.

According to an embodiment, a miniaturized surgical tracking device 1 for treatment of an anatomical structure 9 comprises an element for optical tracking 2, an integrated fiducial marker 4 for direct registration of a radiographic image 13 to the coordinate frame of the tracking device. The tracking device can be fixed to the anatomical structure 9 for radiographic imaging and surgical intervention 5. Surgical instruments 8 can be tracked by the tracking system 2 and their position displayed for images for guided surgical interventions on a display device.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of an element or compound selected from the group consisting of A, B, C . . . and N, the text should be interpreted as requiring only one element from the group, not A plus N, or B plus N, etc.

The invention claimed is:

1. A mobile surgical tracking system comprising a shadow imaging device, a mobile surgical tracking device configured to be mounted on an anatomical structure, an integrated fiducial marker and an integrated optical tracking system, wherein the mobile surgical tracking device includes the shadow imaging device comprising an image sensor and a shadow mask, wherein the shadow imaging device is configured to generate an image of a patient's anatomical structure, the mobile surgical tracking system further comprising a mobile tracking system coordinate frame, wherein the integrated fiducial marker has a position which has a known relation to the mobile tracking system coordinate frame for a direct registration of the image to a coordinate system of the mobile surgical tracking device wherein an instrument can be tracked and visualized by a visualization element in an image space once the relation from the image to the coordinate frame of the mobile surgical tracking device is known, wherein the instrument comprises an optical marker of at least four LEDs.

2. The mobile surgical tracking system according to claim 1 wherein the integrated fiducial marker comprises a computer detectable element, wherein the computer detectable element is detectable in the image, wherein the computer detectable element comprises at least one of spheres, line segments, circles, ellipses, helices, patterns, or holes, and wherein the image comprises an image coordinate frame or an image projection to allow the direct registration of the image coordinate frame or the image projection to the mobile surgical tracking system coordinate frame.

3. The mobile surgical tracking system according to claim 1, wherein the integrated fiducial marker is integrated in a printed circuit board (PCB) containing tracking system electronics, and wherein the printed circuit board (PCB) comprises one of a single PCB, a multi-layer PCB, a plurality of PCBs, or a flexible PCB.

4. The mobile surgical tracking system according to claim 1, wherein the integrated fiducial marker is incorporated into a housing of the mobile surgical tracking device with a known relation to a coordinate frame of an optical tracking element.

5. The mobile surgical tracking system according to claim 1, wherein the integrated fiducial marker is one of integrated into a patient fixation device or attached to the patient fixation device, and wherein the mobile surgical tracking device is configured to be attached to the integrated fiducial marker in a defined spatial position.

6. The mobile surgical tracking system according to claim 5, wherein the patient fixation device has a geometry usable as the integrated fiducial marker, such that the mobile surgical tracking device is configured to be attached in a known position on the mobile surgical tracking device.

7. The mobile surgical tracking system according to claim 1, wherein the integrated optical tracking system comprises a camera system comprising a single camera system, a stereo camera system or a multiple camera system able to track spatial position of passive or active markers.

8. The mobile surgical tracking system according to claim 1 comprising a battery.

9. The mobile surgical tracking system according to claim 1 comprising a display device which is configured to implement wireless communication, wherein the display device is configured to retrieve preoperatively acquired tracking data, image data, planning data or other patient data stored in a memory of the mobile surgical tracking device or the display device comprises an augmented reality display device.

10. The mobile surgical tracking system according to claim 9, wherein the image is configured to be imported to the display device by taking a photo of a C-Arm image with the display device.

11. The mobile surgical tracking system according to claim 1 wherein at least one of the mobile surgical tracking device or a trackable device comprises at least one integrated fiducial marker, wherein the integrated fiducial marker is configured to be attached to an anatomical structure and the mobile surgical tracking device is configured to be attached to a surgical instrument.

12. The mobile surgical tracking system according to claim 1 wherein a plurality of mobile surgical tracking devices is configured to be attached to a plurality of anatomical structures, and wherein each mobile surgical tracking device is configured to be equipped with trackable elements so that each mobile surgical tracking device is configured to act as at least one of a tracker or a trackable device.

13. The mobile surgical tracking system according to claim 1 comprising multiple optical tracking systems integrated to allow measurement in multiple directions, wherein each of the optical tracking systems comprises a measurement volume, wherein at least one of the optical tracking systems is configured to be separate or at least two of the optical tracking systems are configured to be overlapping.

14. The mobile surgical tracking system according to claim 1 wherein the shadow imaging device comprises a radiographic imaging device, and wherein the radiographic imaging device is configured to be equipped with optical markers so that the position of the radiographic imaging device relative to the mobile surgical tracking device can be measured.

* * * * *